United States Patent [19]

Kirsch et al.

[11] Patent Number: 6,139,773
[45] Date of Patent: Oct. 31, 2000

[54] CYCLOHEXANE DERIVATIVES, AND LIQUID-CRYSTALLINE MEDIUM

[75] Inventors: Peer Kirsch, Darmstadt; Kazuaki Tarumi, Seeheim; Joachim Krause, Dieburg, all of Germany

[73] Assignee: Merck Patent Gesellschaft mit Beschrankter Haftung, Germany

[21] Appl. No.: 09/090,337

[22] Filed: Jun. 4, 1998

[30] Foreign Application Priority Data

Jun. 4, 1997 [DE] Germany .................. 197 23 276

[51] Int. Cl.[7] .................. C09K 19/34; C09K 19/30; C09K 19/32
[52] U.S. Cl. .................. 252/299.63; 252/299.61; 252/299.62
[58] Field of Search .................. 252/299.63, 299.61, 252/299.62

[56] References Cited

U.S. PATENT DOCUMENTS

| | | | |
|---|---|---|---|
| 4,510,069 | 4/1985 | Eidenschink et al. | 252/299.61 |
| 4,713,196 | 12/1987 | Praefcke et al. | 252/299.01 |
| 4,830,470 | 5/1989 | Buchecker et al. | 252/299.01 |
| 4,846,998 | 7/1989 | Pohl et al. | 252/299.63 |
| 4,886,620 | 12/1989 | Hopf et al. | 252/299.61 |
| 4,925,278 | 5/1990 | Buchecket et al. | 252/299.01 |
| 4,943,384 | 7/1990 | Sucrow et al . | 252/299.61 |
| 4,985,583 | 1/1991 | Eidenschink et al. | 558/431 |
| 4,986,931 | 1/1991 | Eidenschink et al. | 252/299.63 |
| 5,108,652 | 4/1992 | Eidenschink et al. | 252/299.63 |

FOREIGN PATENT DOCUMENTS 2248059  3/1992  United Kingdom .

OTHER PUBLICATIONS

English Abstract, JP 5229979, 1993.
English Abstract, JP 5125002, 1998.

*Primary Examiner*—C. H. Kelly
*Attorney, Agent, or Firm*—Millen, White, Zelano, & Branigan, P.C.

[57] ABSTRACT

The invention relates to cyclohexane derivatives of the formula I

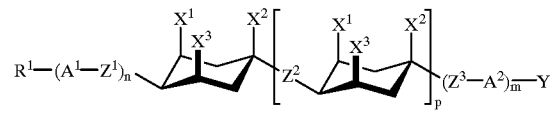

in which n, m, p, $R^1$, $X^1$, $X^2$, $X^3$, $Z^1$, $Z^2$, $Z^3$, $A^1$, $A^2$ and Y are as defined herein.

17 Claims, No Drawings

CYCLOHEXANE DERIVATIVES, AND LIQUID-CRYSTALLINE MEDIUM

The invention relates to novel cyclohexane derivatives of the formula I

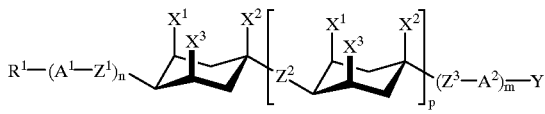

in which

Y is alkyl or alkoxy having 1 to 10 carbon atoms which is unsubstituted or at least monosubstituted by halogen; alkenyl or alkenyloxy having 2 to 10 carbon atoms which is unsubstituted or at least monosubstituted by —CN, —CF$_3$, or —F; or is —CN, —F, —OCHF$_2$, —OCF$_3$, —OCHFCF$_3$ or —OCF$_2$CF$_3$, X$^1$, X$^2$ and X$^3$ are each, independently of one another, H, F, Cl or CN in the axial position, where X$^1$ and X$^3$ are not simultaneously H, R$^1$ is H, an alkyl or alkenyl radical having 1–12 carbon atoms which is unsubstituted, monosubstituted by CN or CF$_3$ or at least monosubstituted by halogen, where one or more non-adjacent CH$_2$ groups in these radicals may also, in each case independently of one another, be replaced by —O—, —S—, —CO—,

—CO—O—, —O—CO— or —O—CO—O—,

A$^1$ and A$^2$, independently of one another,
  a) are a trans-1,4-cyclohexylene radical, in which, in addition, one or more non-adjacent CH$_2$ groups may be replaced by —O— and/or —S—,
  b) are a 1,4-phenylene radical, in which, in addition, one or two CH groups may be replaced by N,
  c) are a radical selected from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl,
  d) are 1,4-cyclohexenylene,
    where the radicals a), b) and d) may be substituted by CN, Cl or F, Z$^1$, Z$^2$ and Z$^3$ are each, independently of one another, —CO—O—, —O—CO—, —CH$_2$O—, —O—, —O—CH$_2$—, —CH$_2$CH$_2$—, —CH═CH—, —C≡C— or a single bond, n and m, independently of one another, are 0, 1, 2 or 3 and p is 0, 1, 2 or 3,
where
  m+n+p is 1,2,3 or 4.

In addition, the invention relates to the use of compounds of the formula I as components of liquid-crystalline media, and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases (DAP) or electrically controlled birefringence (ECB), or the effect of dynamic scattering.

The substances employed hitherto for this purpose all have certain disadvantages, for example inadequate stability to exposure to heat, light or electric fields, or unfavorable elastic and/or dielectric properties.

Compounds containing halocyclohexane units or nitrilo-cyclohexane units are disclosed, for example in JP 05125002, JP 05229979 and EP 0107759, but no compounds of the formula I containing cyclohexane rings with F, Cl or CN as lateral substituents in the axial position are described therein. The laterally substituted cyclohexane derivatives covered by DE 3510432 preferably have equatorial substituents. This document relates to compounds of low viscosity.

The invention had an object of finding novel, stable, liquid-crystalline or mesogenic compounds of negative or slightly positive dielectric anisotropy which are suitable as components of liquid-crystalline media, in particular for TFT and STN displays.

Upon further study of the specification and appended claims, further objects and advantages of this invention will become apparent to those skilled in the art.

It has now been found that the compounds of the formula I are eminently suitable as components of liquid-crystalline media. They can be used to obtain stable liquid-crystalline media, particularly suitable for TFT or STN displays. The novel compounds are distinguished, in particular, by high thermal stability, which is advantageous for a high holding ratio, and exhibit favorable clearing points. Preferred compounds of the formula I have negative dielectric anisotropy and are therefore particularly suitable for displays based on the effect of deformation of aligned phases.

The provision of compounds of the formula I very generally considerably broadens the range of liquid-crystalline substances which are suitable from various applicational points of view for the preparation of liquid-crystalline mixtures.

The compounds of the formula I have a broad range of applications. Depending on the choice of substituents, these compounds can be used as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity. The formula I includes all isotopes of the chemical elements bound in the compounds of the formula I. In enantiomerically pure or enriched form, the compounds of the formula I are also suitable as chiral dopants and in general for achieving chiral mesophases.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I, and to liquid-crystal display elements, in particular electro-optical display elements, which contain media of this type.

Above and below, n, m, p, R$^1$, X$^1$, X$^2$, X$^3$, Z$^1$, Z$^2$, Z$^3$, A$^1$, A$^2$ and Y are as defined above, unless expressly stated otherwise. If the radical X$^1$ appears more than once, it can have identical or different meanings. The same applies to X$^2$, X$^3$, A$^1$, A$^2$, Z$^1$, Z$^2$ and Z$^3$.

For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bco denotes a bicyclo [2.2.2]octylene radical, where Cyc and/or Phe may be unsubstituted or monosubstituted or polysubstituted by Cl, F or CN.

W denotes the following structural unit:

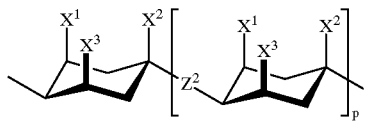

in which p, $X^1$, $X^2$, $X^3$, and $Z^2$ are as defined above.

The formula I covers, among others, compounds of the subformula Ia:

R$^1$—W—Y                  Ia compounds of the subformulae Ib, Ic and Id:

R$^1$—W—A$^2$—Y            Ib

R—W—Z$^3$—A$^2$—Y          Ic

R$^1$—A$^1$—Z$^1$—W—Y      Id compounds of the subformulae Ie to Ii:

R$^1$—W—A$^2$—A$^2$—Y                      Ie

R$^1$—W—A$^2$—Z$^3$—A$^2$—Y                If

R$^1$—W—Z$^3$—A$^2$—A$^2$—Y                Ig

R$^1$—W—Z$^3$—A$^2$—Z$^3$—A$^2$—Y          Ih

R$^1$—A$^1$—Z$^1$—W—A$^2$—Y                Ii and compounds of the subformulae Ij to Ir:

R$^1$—W—A$^2$—A$^2$—A$^2$—Y                        Ij

R$^1$—W—Z$^3$—A$^2$—A$^2$—A$^2$—Y                  Ik

R$^1$—W—A$^2$—Z$^3$—A$^2$—A$^2$—Y                  Il

R$^1$—W—A$^2$—A$^2$—Z$^3$—A$^2$—Y                  Im

R$^1$—W—Z$^3$—A$^2$—Z$^3$—A$^2$—A$^2$—Y            In

R$^1$—W—Z$^3$—A$^2$—A$^2$—Z$^3$—A$^2$—Y            Io

R$^1$—W—A$^2$—Z$^3$—A$^2$—Z$^3$—A$^2$—Y            Ip

R$^1$—W—Z$^3$—A$^2$—Z$^3$—A$^2$—Z$^3$—A$^2$—Y      Iq

R$^1$—A$^1$—Z$^1$—W—A$^2$—Z$^2$—A$^2$—Y            Ir

Of these, particular preference is given to those of the subformulae Ia, Ib, Id, Ie, If, Ih, Ii and Ij.

The preferred compounds of the subformula Ib include those of the subformulae Iba and Ibb:

R$^1$—W—Phe—Y              Iba

R$^1$—W—Cyc—Y              Ibb.

The preferred compounds of the subformula Ic include those of the subformulae Ica and Icb:

R$^1$—W—Z$^3$—Phe—Y        Ica

R$^1$—W—Z$^3$—Cyc—Y        Icb.

The preferred compounds of the subformula Id include those of the subformulae Idb and Idb:

R$^1$—Dio—Z$^1$—W—Y        Ida

R$^1$—Cyc—Z$^1$—W—Y        Idb.

The preferred compounds of the subformula Ie include those of the subformulae Iea to Ieg:

R$^1$—W—Cyc—Cyc—Y          Iea

R$^1$—W—Cyc—Phe—Y          Ieb

R$^1$—W—Phe—Phe—Y          Iec

R$^1$—W—Pyd—Phe—Y          Ied

R$^1$—W—Phe—Cyc—Y          Iee

R$^1$—W—Dio—Phe—Y          Ief

R$^1$—W—Pyr—Phe—Y          Ieg

Of these, those of the formulae Iea, Ieb, Iec and Iee are particularly preferred.

The preferred compounds of the subformula If include those of the subformulae Ifa to Ifg:

R$^1$—W—Cyc—Z$^3$—Cyc—Y            Ifa

R$^1$—W—Cyc—Z$^3$—Phe—Y            Ifb

R$^1$—W—Phe—Z$^3$—Phe—Y            Ifc

R$^1$—W—Pyr—Z$^3$—Phe—Y            Ifd

R$^1$—W—Pyd—Z$^3$—Phe—Y            Ife

R$^1$—W—Cyc—CH$_2$—CH$_2$—Phe—Y    Iff

R$^1$—W—A$^2$—CH$_2$CH$_2$—Phe—Y   Ifg.

Preferred compounds of the subformula Ig include those of the subformulae Iga to Igh:

R$^1$—W—Z$^3$—Cyc—Cyc—Y            Iga

R$^1$—W—CH$_2$CH$_2$—A$^2$—A$^2$—Y Igb

R$^1$—W—Z$^3$—Cyc—Phe—Y            Igc

R$^1$—W—OCO—A$^2$—Phe—Y            Igd

R$^1$—W—Z$^3$—Phe—Phe—Y            Ige

R$^1$—W—Z$^3$—Pyr—A$^2$—Y          Igf

R$^1$—W—Z$^3$—Pyd—A$^2$—Y          Igg

R$^1$—W—Z$^3$—Dio—A$^2$—Y          Igh.

Of these, those of the subformulae Iga, Igb, Igc and Ige are particularly preferred.

The preferred compounds of the subformula Ih include those of the subformulae Iha to Ihe:

R$^1$—W—CH$_2$CH$_2$—Phe—Z$^3$—A$^2$—Y      Iha

R$^1$—W—COO—A$^2$—Z$^3$—Phe—Y               Ihb

R¹—W—Z³—Cyc—Z³—Cyc—Y          Ihc

R¹—W—Z³—Phe—Z³—Phe—Y          Ihd

R¹—W—CH₂CH₂—Cyc—Z³—Phe—Y      Ihe.

The preferred compounds of the subformula Ii include those of the subformulae Iia to Iie:

R¹—CH₂CH₂—W—Phe—Y             Iia

R¹—Dio—W—Phe—Y                Iib

R¹—Phe—W—Cyc—Y                Iic

R¹—Cyc—W—Cyc—Y                Iid

R¹—Dio—CH₂CH₂—W—Cyc—Y         Iie.

The preferred compounds of the subformulae Ij to Ir include those of the subformulae Is to Iz:

R¹—W—A²—Cyc—Cyc—Y             Is

R¹—W—A²—Cyc—Phe—Y             It

R¹—W—A²—CH₂CH₂—A²—Phe—Y       Iu

R¹—W—Z³—Cyc—Z³—A²—Phe—Y       Iv

R¹—W—Phe—Phe—Phe—Y            Iw

R¹—W—Phe—Z³—A²—Phe—Y          Ix

R¹—W—A²—Phe—Z³—Phe—Y          Iy

R¹—W—Z³—A²—Cyc—Z³—Phe—Y       Iz.

Y is preferably —CN, —F, —OCF₃, straight-chain alkyl or alkoxy having 1 to 10 carbon atoms or alkenyl or alkenyloxy having 2 to 10 carbon atoms, in particular CN, F, alkyl, alkoxy or alkenyl. Very particular preference is given to alkyl and alkoxy.

The preferred meaning of $X^1$, $X^2$ and $X^3$ is F or CN, in particular F.

In the compounds of the formulae above and below, R¹ is preferably straight-chain alkyl having 1 to 10 carbon atoms or alkenyl having 2 to 10 carbon atoms, furthermore preferably alkoxy having 1 to 10 carbon atoms.

A¹ is preferably Phe, Cyc, Che, Pyd, Pyr or Dio, in particular Cyc or Dio. The compounds of the formula I preferably contain not more than one of the radicals Bco, Pyd, Pyr, Dio and Dit.

Preference is also given to compounds of the formula I and all subformulae in which A¹ is 1,4-phenylene which is monosubstituted or disubstituted by F or CN.

A¹ is preferably

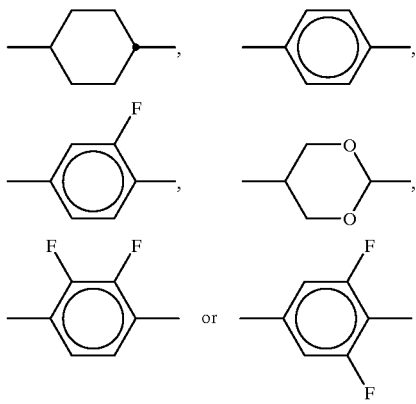

n is preferably 0 or 1, particularly preferably 0. m and p are preferably 0, 1 or 2, particularly preferably 0 or 1. $Z^1$, $Z^2$ and $Z^3$, independently of one another, are preferably —CH₂CH₂—, —CH=CH— or a single bond, particularly preferably a single bond or —CH₂—CH₂—.

Preference is given to compounds of the formula I in which R¹ and Y are simultaneously alkyl having 1 to 10 carbon atoms, while n is 0 and m is 1.

Particular preference is furthermore given to compounds of the formula I which are characterized in that R¹ is straight-chain alkyl or alkoxy having 1 to 10 carbon atoms or alkenyl having 2 to 10 carbon atoms, and Y is alkyl having 1 to 10 carbon atoms, alkenyl having 2 to 10 carbon atoms, and Y is alkyl having 1 to 10 carbon atoms, alkenyl having 2 to 10 carbon atoms, —CN, —F, —OCHF₂ or —OCF₃.

The 1,4-cyclohexenylene group preferably has one of the following structures:

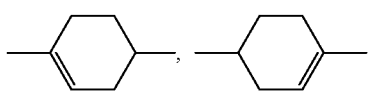

The following group of compounds of the subformulae I1 to I37 represents a further preferred embodiment of the invention:

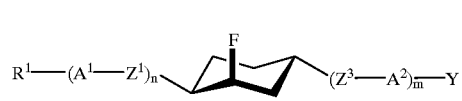
I1

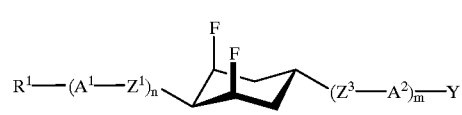
I2

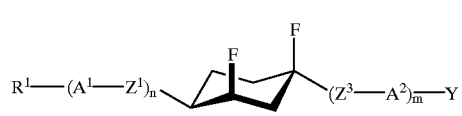
I3

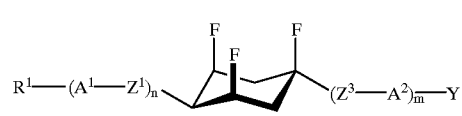
I4

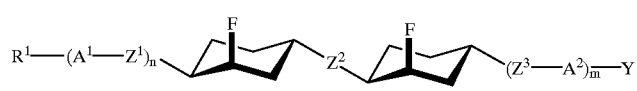
I5

I6
I7
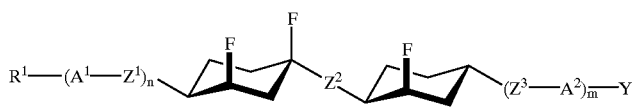
I8
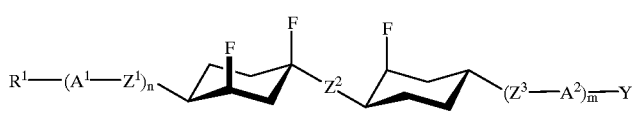
I9
I10
I11
I12
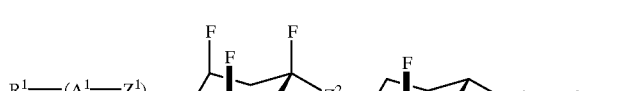
I13
I14
I15
I16
I17
I18

-continued
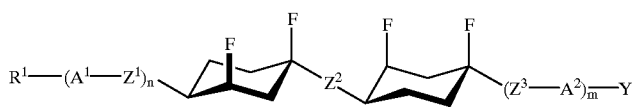
I19
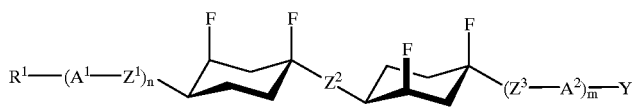
I20
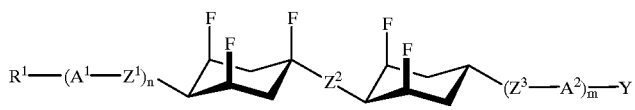
I21
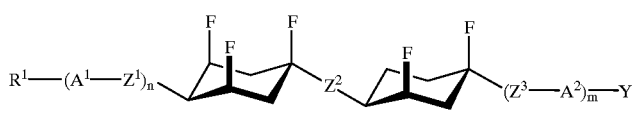
I22
I23
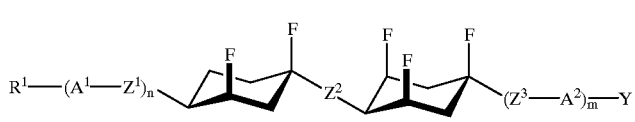
I24
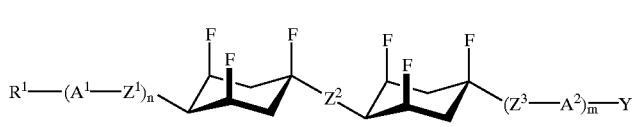
I25
I26
I27
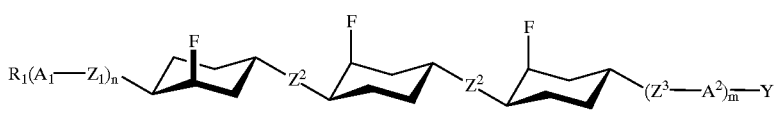
I28
I29
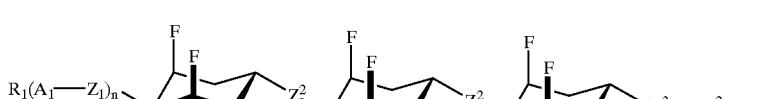
I30
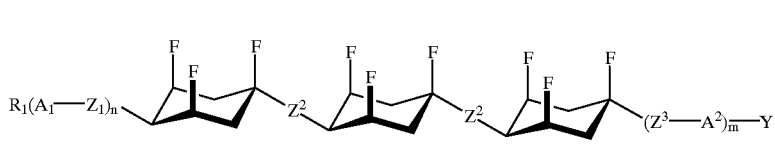
I31

-continued
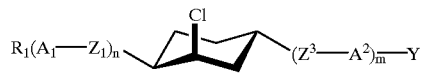
I32
I33
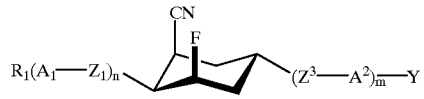
I34
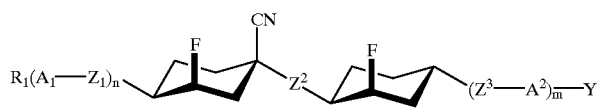
I35
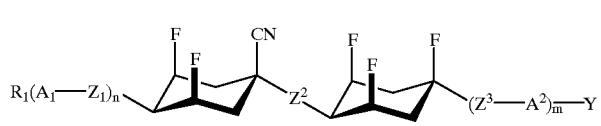
I36
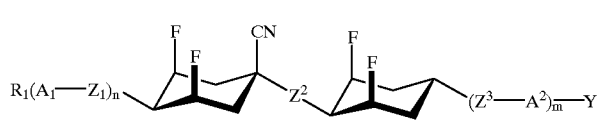
I37
in which n, m, $R^1$, $Z^1$, $Z^2$, $Z^3$, $A^1$, $A^2$ and Y are as defined above.
Particular preference is furthermore given to the compounds of the formulae I38 to I89 in the following group:
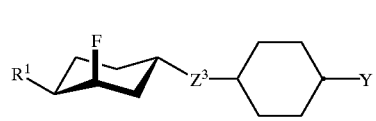
I38
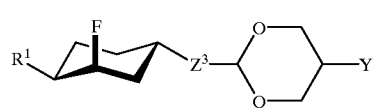
I39
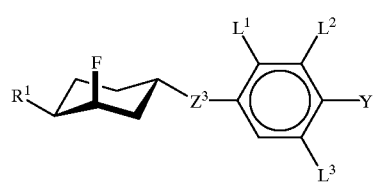
I40
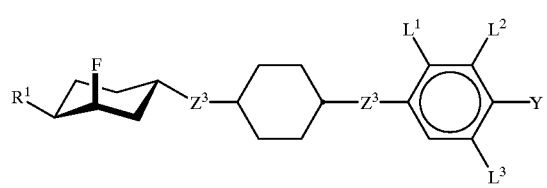
I41
I42

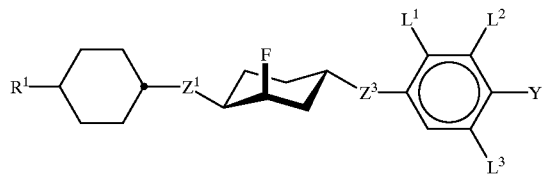
I43
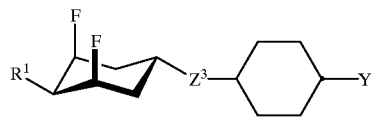
I44
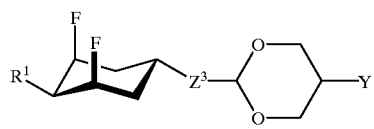
I45
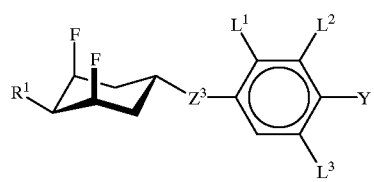
I46
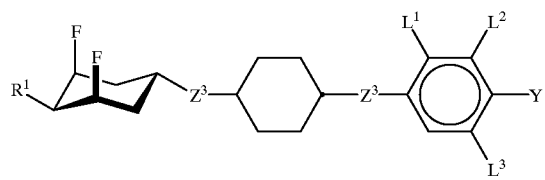
I47
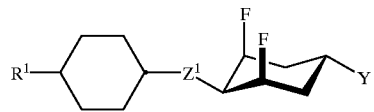
I48
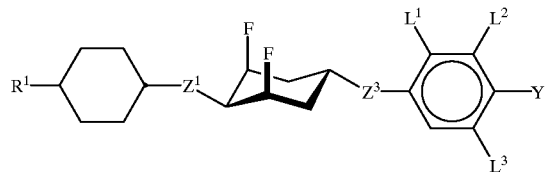
I49
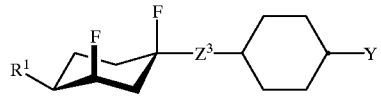
I50
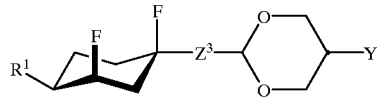
I51
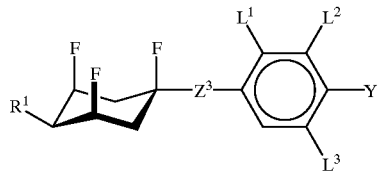
I52

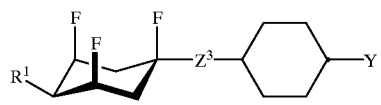
I53
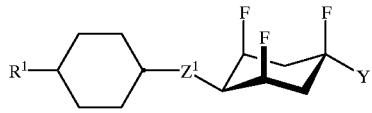
I54
I55
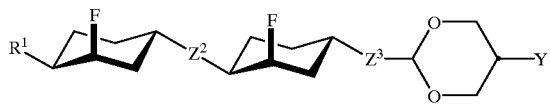
I56
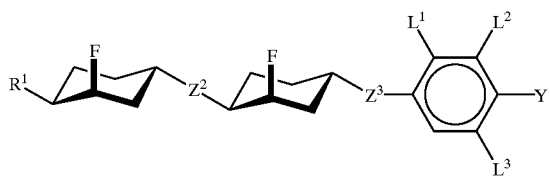
I57
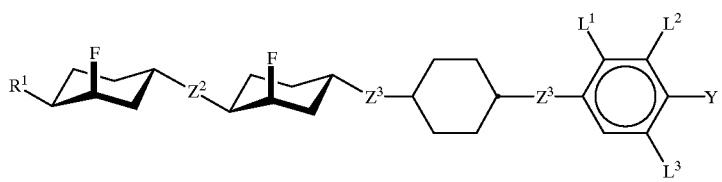
I58
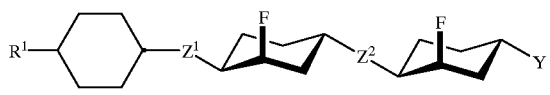
I59
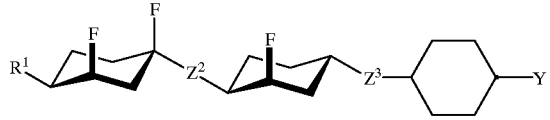
I60
I61
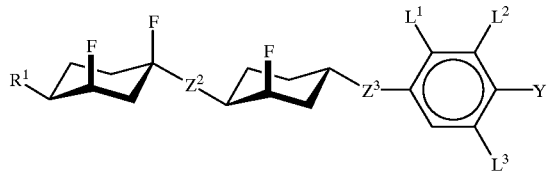
I62

I63
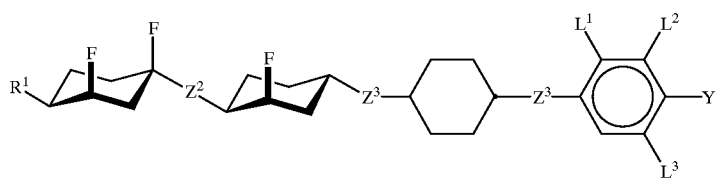
I64
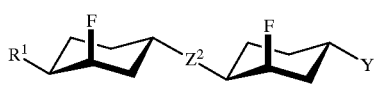
I65
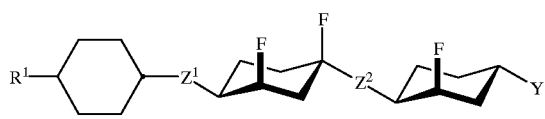
I66
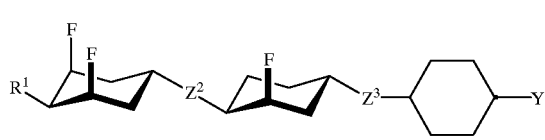
I67
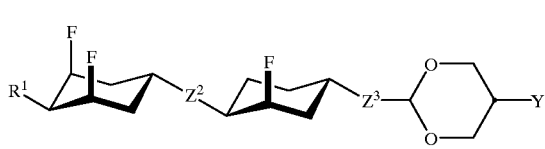
I68
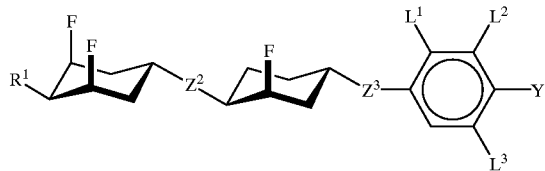
I69
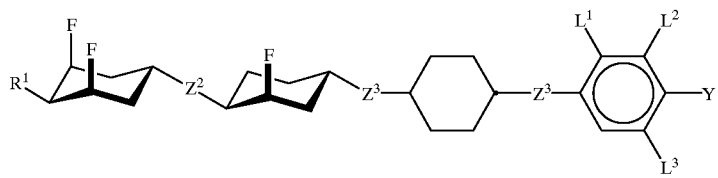
I70
I71
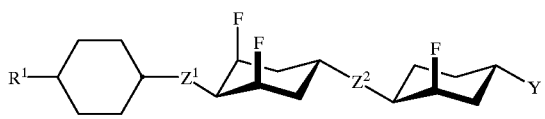
I72
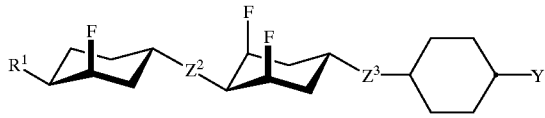

-continued
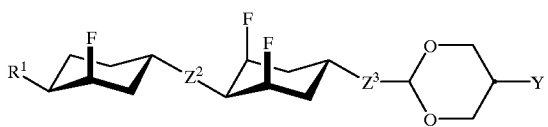
I73
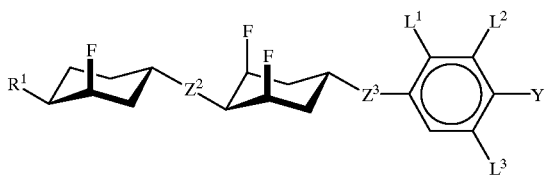
I74
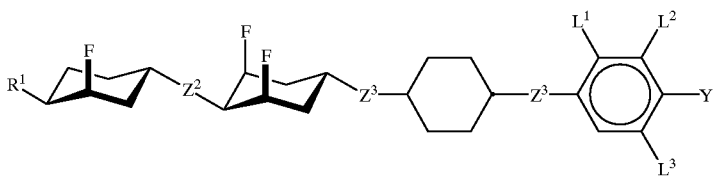
I75
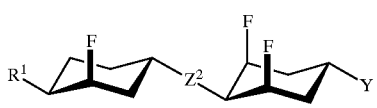
I76
I77
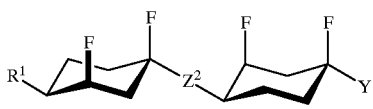
I78
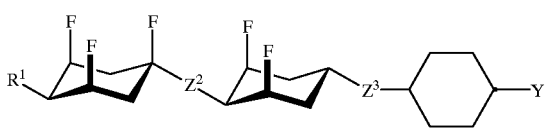
I79
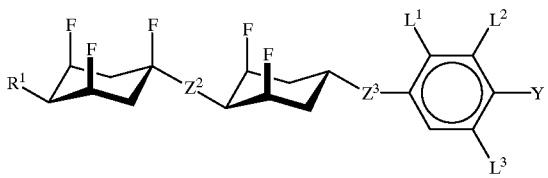
I80
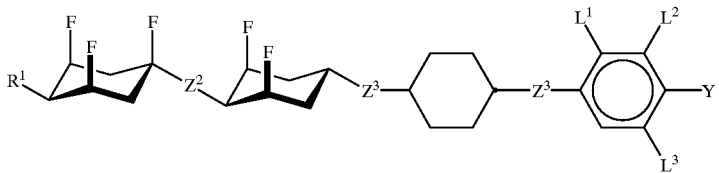
I81
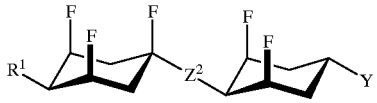
I82

-continued

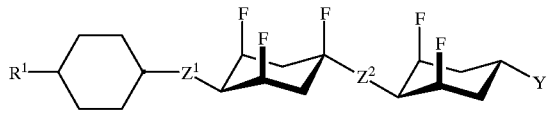
I83

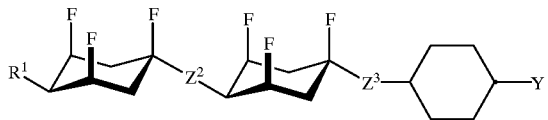
I84

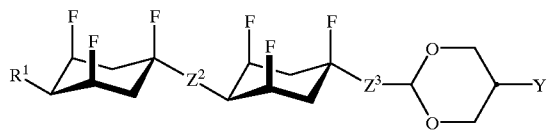
I85

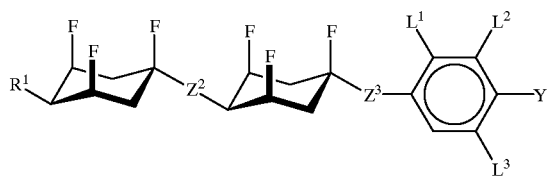
I86

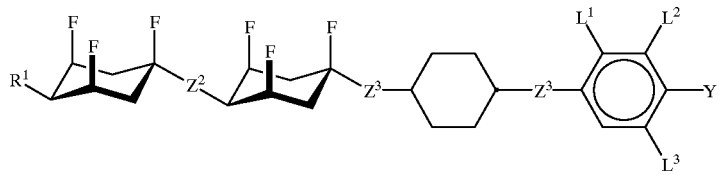
I87

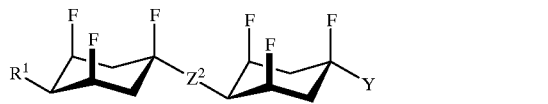
I88

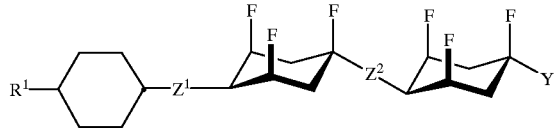
I89 in which $R^1$, $Z^1$, $Z^2$, $Z^3$ and Y are as defined above, $L^1$, $L^2$ and $L^3$ are each, independently of one another, F or H, $L^1$ and $L^2$ are preferably F and $L^3$ is preferably H.

If $R^1$ in the formulae above and below is an alkyl radical and/or alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (= methoxymethyl), 2- (= ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ is an alkyl radical in which one $CH_2$ group has been replaced by —CH=CH—, this can be straight-chain or branched. It is preferably straight-chain and has 2 to 10 carbon atoms. Accordingly, it is in particular vinyl, prop 1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ is an alkyl radical in which one $CH_2$ group has been replaced by —O— and one has been replaced by —CO—, these are preferably adjacent. These thus contain one acyloxy group —CO—O— or one oxycarbonyl group —O—CO—. These are preferably straight-chain and have 2 to 6 carbon atoms.

Acccordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R¹ is an alkyl radical in which one CH₂ group has been replaced by unsubstituted or substituted —CH═CH— and an adjacent CH₂ group has been replaced by CO or CO—O or O—CO—, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7l-methacryloyloxyheptyl, 8-methacryloyloxyoctyl and 9-methacryloyloxynonyl.

If R¹ is an alkyl or alkenyl radical which is monosubstituted by CN or CF₃, this radical is preferably straight-chain, and the substitution by CN or CF₃ is in the ω-position.

If R¹ is an alkyl or alkenyl radical which is at least monosubstituted by halogen, this radical is preferably straight-chain, and halogen is preferably F or Cl. In the case of multiple substitution, halogen is preferably F. The resulting radicals also include perfluorinated radicals. In the case of monosubstitution, the fluorine or chlorine substituent can be in any desired position, but is preferably in the ω-position.

Compounds of the formula I containing branched wing groups R¹ may occasionally be of importance due to better solubility in the customary liquid-crystalline base materials, but in particular as chiral dopes if they are optically active. Smectic compounds of this type are suitable as components for ferroelectric materials.

Branched groups of this type generally contain not more than one chain branch. Preferred branched radicals R are isopropyl, 2-butyl (=1-methoylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The formula I covers the racemates of these compounds and the optical antipodes, and mixtures thereof.

Of these compounds of the formula I and the subformulae, preference is given to those in which at least one of the radicals present therein has one of the preferred meanings indicated.

In the compounds of the formula I, preference is given to the stereoisomers in which the rings Cyc and piperidine are trans-1,4-disubstituted. Those of the abovementioned formulae which contain one or more groups Pyd, Pyr and/or Dio in each case include the two 2,5-positional isomers.

Some very particularly preferred smaller groups of compounds of the formula I are those of the subformulae I90 to I99:

I90

I91

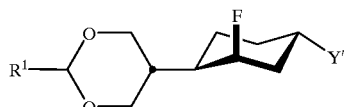

I92

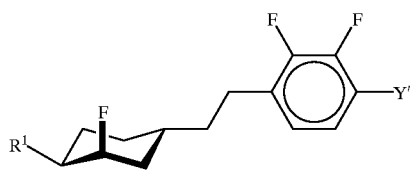

I93

I94

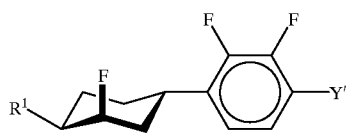

I95

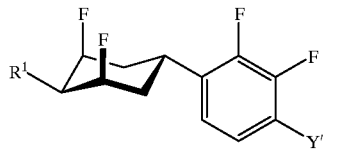

I96

I97

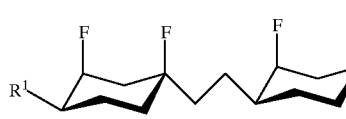

I98

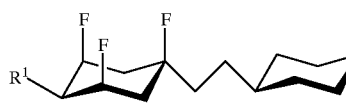

I99

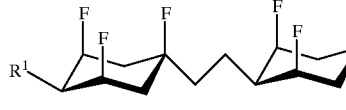

in which R¹ is as defined above, and Y' is alkyl, alkoxy, alkenyl or alkenyloxy.

Very particularly preferred compounds from this group are those of the formulae I90, I91, I92, I94, I96 and I98.

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions.

Use can also be made here of variants which are known per se, but are not described here in greater detail.

The novel axially fluorinated compounds of the formula I can be synthesized using hydrogen fluoride under pressure or by means of amine/hydrogen fluoride adducts (for example A. V. Grosse, C. B. Linn, J. Org. Chem. 3, (1938) 26; G. A. Olah, M. Nojima, I. Kerekes, Synthesis, (1973) 779; G. A. Olah, X-Y. Li, Q. Wang, G. K. S. Prakash, Synthesis (1993) 693).

The compounds according to the invention can be prepared, for example, in accordance with the following reaction schemes:

Scheme 1

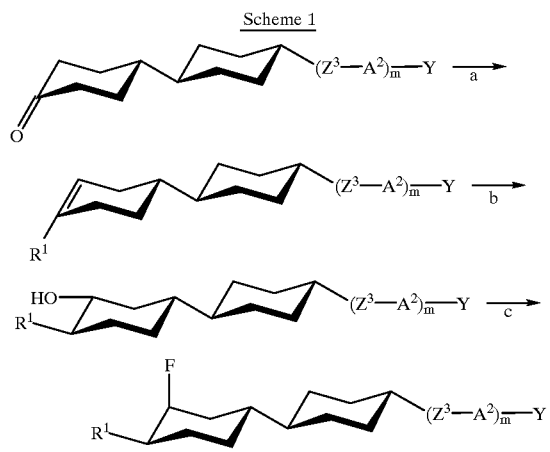

a) 1. R¹MgBr, THF;
   2. toluene, cat. TsOH, water separator
b) 1. THF/BH₃
   2. NaOH, H₂O₂
c) DAST, CH₂Cl₂

Scheme 2

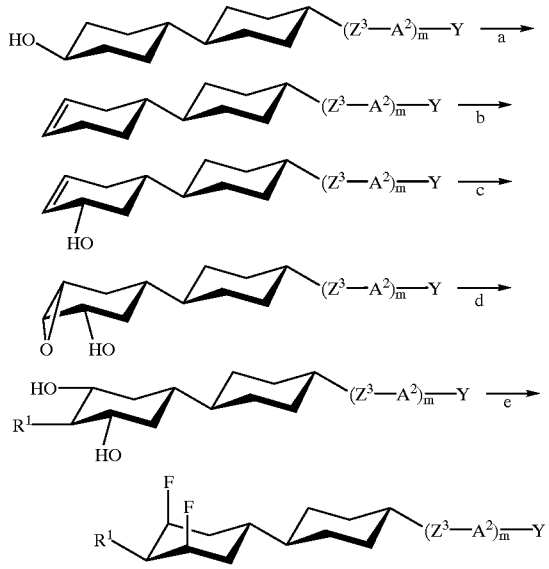

a) 1. toluene, cat. TsOH, water separator
b) 1. NBS, CCl, cat. dibenzoyl peroxide
   2. K₂CO₃, H₂O, acetone
c) MCPBA, CH₂Cl₂
d) R¹MgBr, cat. CuI, THF
e) DAST, CH₂Cl₂

Scheme 3

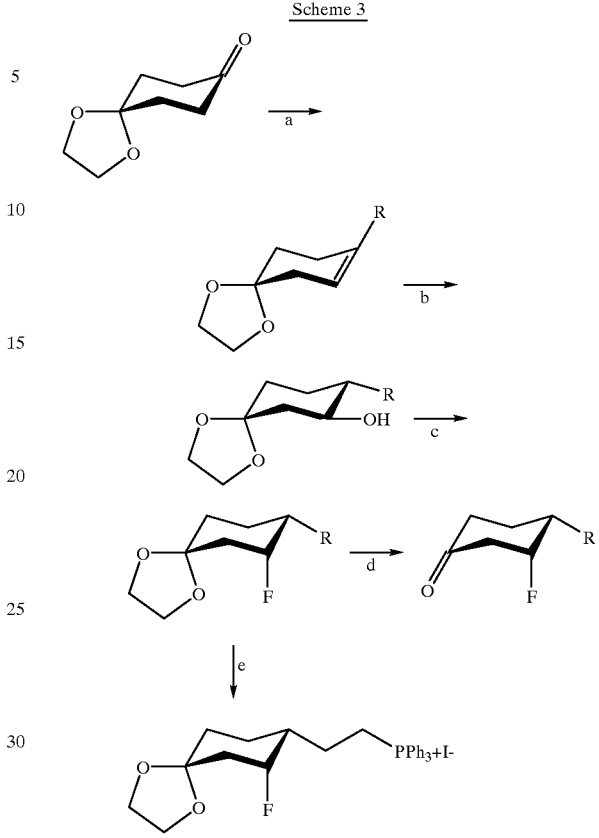

a) 1. RMgBr, THF
   2. toluene, cat. TsOH, water separator
b) 1. THF/BH₃
   2. NaOH, H₂O₂
c) DAST, CH₂Cl₂
d) 98% HCOOH, toluene
e) R = CH₂CH₂OBn
   1. H₂, Pd—Cl, THF
   2. MsCl, CH₂Cl₂, NEt₃
   3. KI, acetone
   4. PPh₃, acetonitrile Scheme 4

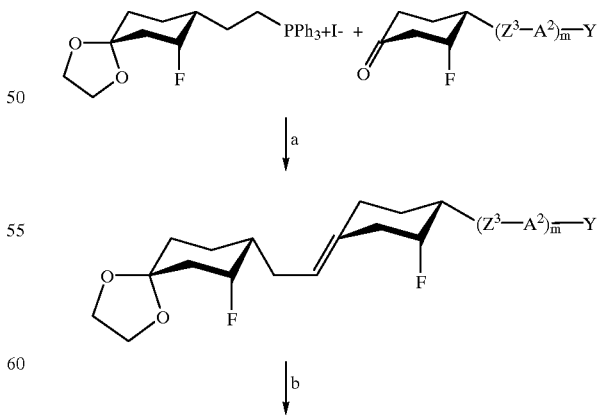

27
-continued

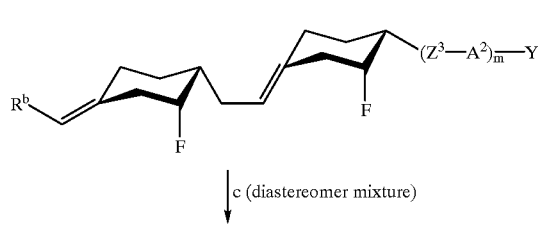

↓ c (diastereomer mixture)

28
-continued

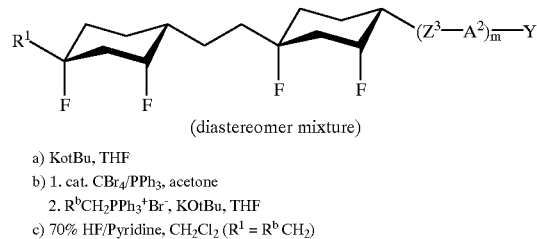

(diastereomer mixture)

a) KOtBu, THF
b) 1. cat. CBr$_4$/PPh$_3$, acetone
   2. R$^b$CH$_2$PPh$_3{}^+$Br$^-$, KOtBu, THF
c) 70% HF/Pyridine, CH$_2$Cl$_2$ (R$^1$ = R$^b$CH$_2$)

Scheme 5

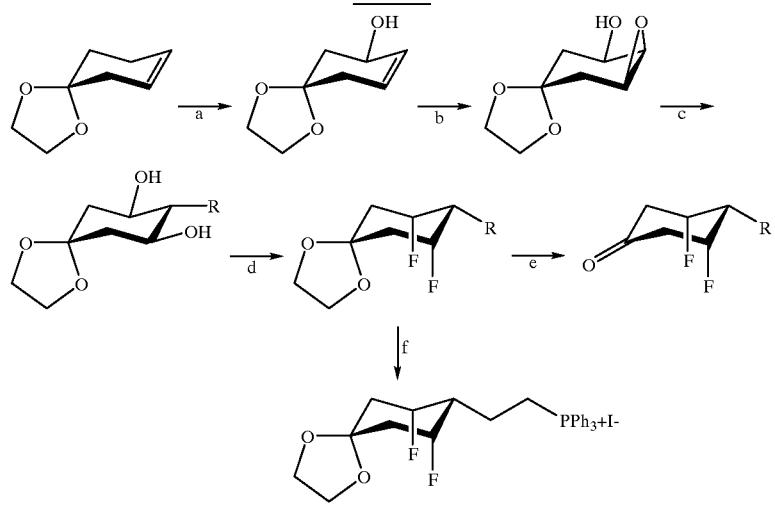

a) 1. NBS, CCl$_4$, cat. dibenzoyl peroxide
   2. K$_2$CO$_3$, H$_2$O, acetone
b) MCPBA, CH$_2$Cl$_2$
c) RMgBr, cat. CuI, THF
d) DAST, CH$_2$Cl$_2$
e) 98% HCOOH, toluene
f) R = CH$_2$CH$_2$OBn
   1. H$_2$, Pd—C, THF
   2. MsCl, CH$_2$Cl$_2$, NEt$_3$
   3. KI, acetone
   4. PPh$_3$, acetonitrile Scheme 6

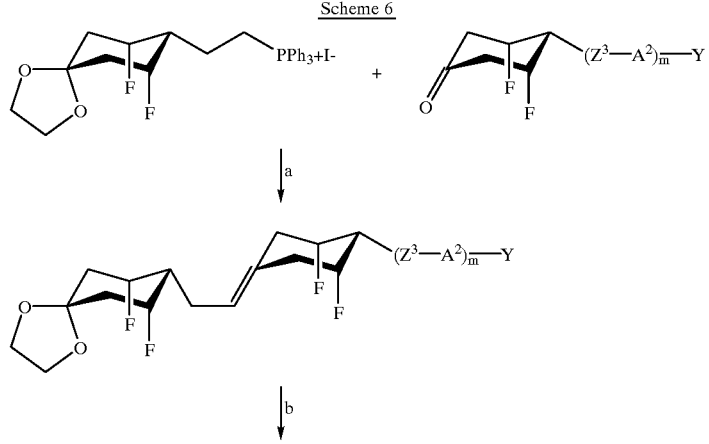

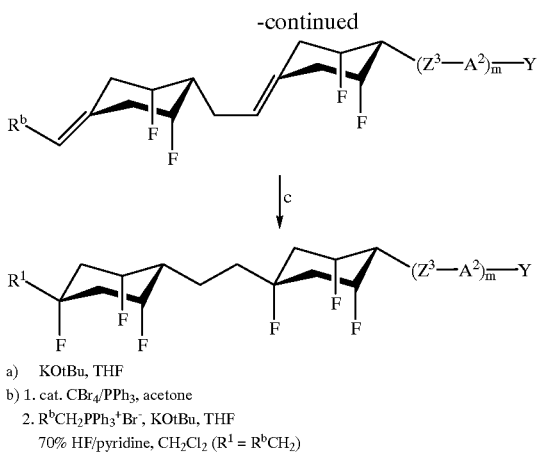

a) KOtBu, THF
b) 1. cat. CBr$_4$/PPh$_3$, acetone
   2. R$^b$CH$_2$PPh$_3^+$Br$^-$, KOtBu, THF
   70% HF/pyridine, CH$_2$Cl$_2$ (R$^1$ = R$^b$CH$_2$)

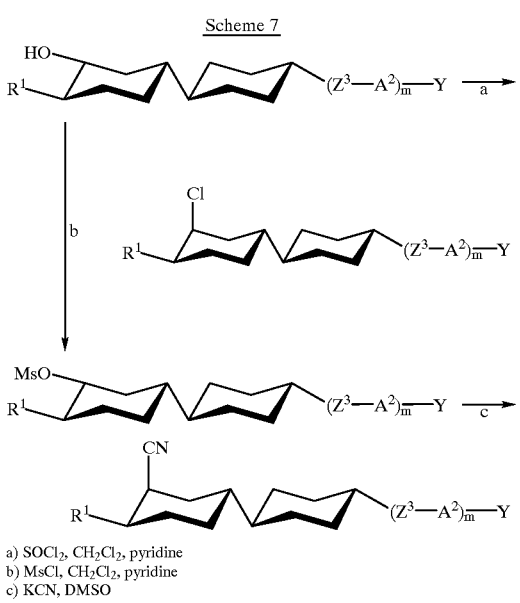

Scheme 7 a) SOCl$_2$, CH$_2$Cl$_2$, pyridine
b) MsCl, CH$_2$Cl$_2$, pyridine
c) KCN, DMSO

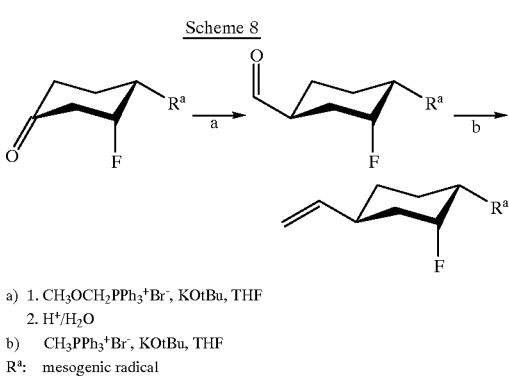

Scheme 8 a) 1. CH$_3$OCH$_2$PPh$_3^+$Br$^-$, KOtBu, THF
   2. H$^+$/H$_2$O
b) CH$_3$PPh$_3^+$Br$^-$, KOtBu, THF
R$^a$: mesogenic radical Esters of the formula I can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known or can be prepared analogously to known processes.

Nitriles can be obtained by replacing halogens by copper cyanide or alkali metal cyanide.

In a further process for the preparation of compounds of the formula I in which $Z^1$, $Z^2$ or $Z^3$ is —CH=CH—, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines which are necessary for the success of the coupling reaction, such as, for example, triethylamine, are also suitable as solvent. Examples of suitable palladium catalysts are palladium salts, in particular Pd(II) acetate, and organophosphorous(III) compounds, such as, for example, triarylphosphines. Reaction can be carried out in the presence or absence of an inert solvent, at temperatures between 0° C. and 150° C., preferably between 20° C. and 100° C.; examples of suitable solvents are nitriles, such as acetonitrile, or hydrocarbons, such as benzene or toluene. The aryl halides and olefins employed as starting materials are frequently commercially available or can be prepared by processes known from the literature, for example by halogenation of corresponding parent compounds or by elimination reactions on corresponding alcohols or halides.

In this way, for example, stilbene derivatives can be prepared. Stilbenes can furthermore be prepared by reacting a 4-substituted benzaldehyde with a corresponding phosphorous ylide by the Wittig method. However, it is also possible to prepare tolans of the formula I by using monosubstituted acetylene instead of the olefin (Synthesis 627 (1980) or Tetrahedron Lett. 27, 1171 (1986).

Furthermore, the coupling of aromatic compounds can be carried out by reacting aryl halides with aryltin compounds. These reactions are preferably carried out with addition of a catalyst, such as, for example, a palladium (0) complex, in inert solvents, such as hydrocarbons, at high temperatures, for example in boiling xylene under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I in which $Z^1$ or $Z^2$ is —C≡C— can also be prepared by Fritsch-Buttenberg-Wiechell rearrangement (Ann. 279, 319, 1984), in which 1,1-diaryl-2-haloethylenes are rearranged in the presence of strong bases to give diarylacetylenes.

Tolans of the formula I can also be prepared by brominating the corresponding stilbenes, and then subjecting the products to dehydrohalogenation. Use can also be made here of variants of this reaction which are known per se, but are not mentioned here in greater detail.

Ethers of the formula I are obtainable by esterification of corresponding hydroxyl compounds, preferably corresponding phenols, where the hydroxyl compound is advantageously first converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This alkoxide or phenoxide can then be reacted with the appropriate alkyl halide, alkyl sulphonate or dialkyl sulphate, advantageously in an inert solvent, such as, for example, acetone, 1,2-dimethoxyethane, DMF or di-methyl sulphoxide, or alternatively with an excess of aqueous or aqueous-alcoholic NaOH or KOH, at temperatures between about 20° C. and 100° C.

The starting materials are either known or can be prepared analogously to known compounds.

The liquid-crystalline media according to the invention preferably comprises from 2 to 40, in particular from 4 to 30, components as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)-ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

R'—L—E—R"  (1)

R'—L—COO—E—R"  (2)

R'—L—OOC—E—R"  (3)

R'—L—CH$_2$CH$_2$—E—R"  (4)

R'—L—C≡C—E—R"  (5)

In the formulae 1, 2, 3, 4, and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cc, Phe or Phe-Cyc. The media according to the invention preferably comprises one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group consisting of —Phe—Cyc—, —Cyc—Cyc—, —G—Phe— and —G—Cyc—.

In a smaller sub-group of the compounds of the formulae 1,2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labeled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+1)}$F$_k$Cl$_1$, where i is 0 or 1, and k and l are 1, 2 or 3; the compounds in which R" has this meaning are labeled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably Group A: from 0 to 90%, preferably from 20 to 90%, in particular from 30 to 90%

Group B: from 0 to 80%, preferably from 10 to 80%, in particular from 10 to 65%

Group C: from 0 to 80%, preferably from 5 to 80%, in particular from 5 to 50%, the sum of the proportions by weight of the group A and/or B and/or C compounds present in the particular media according to the invention preferably being 5%–90% and in particular from 0% to 90%.

The media according to the invention preferably comprise from 1 to 40%, particularly preferably from 5 to 30%, of compounds according to the invention. Further preferred media are those which comprise more than 40%, in particular from 45 to 90%, of compounds according to the invention. The media preferably comprise three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

The entire disclosure of all applications, patents and publications, cited above and below, and of corresponding German application No. 197 23 276.0, filed Jun. 4, 1997 is hereby incorporated by reference.

EXAMPLES

The examples below are intended to illustrate the invention without representing a limitation. Above and below, percent data are percent by weight. All temperatures are given in degrees Celsius. m.p.=melting point, cl.p.=clearing point. Furthermore, C=crystalline state, N=nematic phase, S=smectic phase and I=isotropic phase. The number between two symbols indicates the conversion temperature in degrees Celsius. Δn denotes optical anisotropy (589 nm, 20° C.). The viscosity (mm²/sec) was determined at 20° C.

"Conventional work-up" means that water is added if necessary, the mixture is extracted with methylene chloride, diethyl ether, or toluene, the organic phase is separated off, dried and evaporated, and the product is purified by distillation under reduced pressure or crystallization and/or chromatography.

The following abbreviations are used:

| | |
|---|---|
| THF | tetrahydrofuran |
| KOtBu | potassium tert-butoxide |
| RT | room temperature |
| MTB ether | methyl tert-butyl ether |

Example 1

4'-Pentyl-4-propylbicyclohexyl-4-ol

A suspension of 21.9 g of magnesium turnings in 200 ml of THF was warmed to 60° C., and 10% of a solution of 80 ml of bromopropane in 200 ml of THF was added dropwise. When the reaction commenced, the remainder of the solution was added dropwise over the course of 30 minutes under reflux. The mixture was stirred at 70° C. for a further hour.

200 g of 4'-pentylbicyclohexyl-4-one were dissolved in 400 ml of THF and added dropwise under reflux. The mixture was stirred for a further 30 minutes, cooled to RT and hydrolyzed using dilute hydrochloric acid.

The batch was taken up in MTB ether. The aqueous phase was separated off, and the organic phase was washed twice with water. The aqueous phase was washed twice with water. The aqueous phase was extracted again with MTB ether. The combined organic phases were dried using sodium sulphate, filtered and evaporated to give a residue, giving 4'-pentyl-4-propylbicyclohexyl-4-ol.

Example 2

4'-Pentyl-4-propylbicyclohexyl-3-ene 236.0 g of 4'-pentyl-4-propylbicyclohexyl-4-ol, 1.5 l of toluene and 5 ml of sulphuric acid were refluxed for 1.5 hours on a water separator. The mixture was subsequently cooled to RT, and washed with saturated sodium hydrogen carbonate solution and then with water. The aqueous phase was separated off and extracted with toluene. The combined organic phases were evaporated.

The crude product was dissolved in hexane and filtered through a silica-gel column. The fraction obtained was evaporated and subjected to vacuum distillation, giving 4'-pentyl-4-propylbicyclohexyl-3-ene having a boiling point of 148° C. at 0.1 mbar.

Example 3

4'-Pentyl-4-propylbicyclohexyl-3-ol 56.0 g of 4'-pentyl-4-propylbicyclohexyl-3-ene were dissolved in 500 ml of THF, and the solution was cooled to +2° C. 220 ml of borane/THF complex (1M) were then added dropwise over the course of 30 minutes with stirring. The mixture was stirred at +2° C. for a further hour and again stirred at RT for one hour. 54 ml of ethanol were then added dropwise, during which the solution warmed. A solution of 12 g of sodium hydroxide in 40 ml of water was then added dropwise. 72 ml of a 30% hydrogen peroxide solution were then added dropwise, and the mixture was refluxed for 2 hours with stirring and then cooled again to RT. 250 ml of water were then added, and the mixture was stirred for 20 minutes. The aqueous phase was separated off and extracted twice with MTB ether. The combined organic phases were washed with saturated sodium hydrogencarbonate solution and then with water, dried over sodium sulphate, filtered and evaporated to give a residue. The crude product was dissolved in heptane/MTB ether and filtered through a silica-gel column. A small fraction was separated off at the beginning and discarded. Crystallization of the main fraction gave 4'-pentyl-4-propylbicyclohexyl-3-ol.

Example 4

3-Fluoro-4'-pentyl-4-propylbicyclohexyl 17.5 g of 4'-pentyl-4-propylbicyclohexyl-3-ol were dissolved in 700 ml of dichloromethane. The mixture was then cooled to −20° C., and a solution of 10.0 ml of diethylaminosulphur trifluorode in 30 ml of dichloromethane was added dropwise over the course of about 20 minutes at −20° C. The mixture was stirred for a further 3 hours. The solution was then washed twice with a saturated sodium hydrogen carbonate solution and then with water, dried using sodium sulphate and evaporated to a residue. The residue was taken up in acetone, potassium permanganate was added, and the mixture was stirred at 0° C. for 1.5 hours. Water was added to the solution, and the mixture was extracted with heptane. The organic phase was dried and evaporated to a residue. The residue was recrystallized from heptane, giving 3-fluoro-4'-pentyl-4-propylbicyclohexyl (C 3 SmB 67 I, Δε: −0.9, Δn: 0.046).

The following compounds according to the invention were obtained analogously from the corresponding precursors:

Examples 5–19

| | R¹ | Z³ | A² | Y |
|---|---|---|---|---|
| (5) | n-Propyl | — | 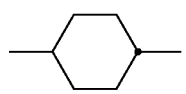 | n-Propyl |
| (6) | n-Propyl | —CH₂—CH₂— | 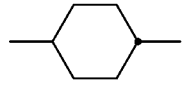 | n-Pentyl |
| (7) | n-Pentyl | — | 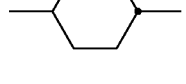 | n-Propyl |
| (8) | n-Pentyl | —CH₂—CH₂— | 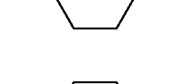 | n-Pentyl |
| (9) | n-Pentyl | — | 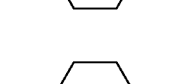 | n-Butyl |
| (10) | n-Pentyl | — | 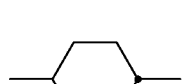 | O-n-Propyl |
| (11) | n-Pentyl | — | 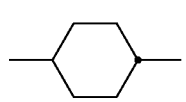 | CH=CH₂ |
| (12) | n-Propyl | — | 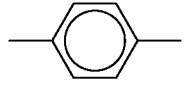 | trans-(CH₂)₂CH=CHCH₃ |
| (13) | n-Propyl | — | 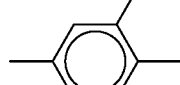 | CH=CH₂ |
| (14) | n-Propyl | — | 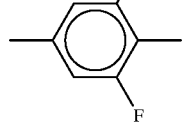 | F |

-continued

[Structure: cyclohexane with F (axial up) at position bearing R¹, and Z³—A²—Y substituent]

| | R¹ | Z³ | A² | Y |
|---|---|---|---|---|
| (15) | n-Pentyl | — | 3,5-difluorophenylene | CN |
| (16) | n-Propyl | —CH₂—CH₂— | 2,3-difluorophenylene | OCF₃ |
| (17) | n-Pentyl | —COO— | phenylene | CN |
| (18) | n-Pentyl | —CH₂—CH₂— | 3-fluorophenylene | F |
| (19) | n-Propyl | —CH₂—CH₂— | phenylene | O-n-Propyl |

Examples 20–34

[Structure: cyclohexane with F substituent, R¹ and Z³—A²—Y groups]

| | R¹ | Z³ | A² | Y |
|---|---|---|---|---|
| (20) | n-Propyl | — | cyclohexylene | n-Propyl |
| (21) | n-Propyl | —CH₂—CH₂— | cyclohexylene | n-Pentyl |
| (22) | n-Pentyl | — | cyclohexylene | n-Propyl |
| (23) | n-Pentyl | —CH₂—CH₂— | cyclohexylene | n-Pentyl |

-continued
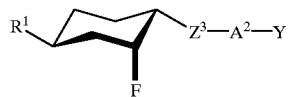
| | R¹ | Z³ | A² | Y |
|---|---|---|---|---|
| (24) | n-Pentyl | — | cyclohexyl | n-Butyl |
| (25) | n-Pentyl | — | cyclohexyl | O-n-Propyl |
| (26) | n-Pentyl | — | cyclohexyl | CH=CH₂ |
| (27) | n-Propyl | — | cyclohexyl | trans-(CH₂)₂CH=CHCH₃ |
| (28) | n-Propyl | — | phenyl | CH=CH₂ |
| (29) | n-Propyl | — | 2,3-difluorophenyl | F |
| (30) | n-Pentyl | — | 2,3-difluorophenyl | CN |
| (31) | n-Propyl | —CH₂—CH₂— | 2,3-difluorophenyl | OCF₃ |
| (32) | n-Pentyl | —COO— | phenyl | CN |
| (33) | n-Pentyl | —CH₂—CH₂— | 3-fluorophenyl | F |

-continued
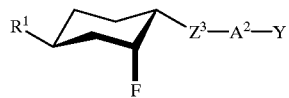
| | R¹ | Z³ | A² | Y |
|---|---|---|---|---|
| (34) | n-Propyl | —CH₂—CH₂— | ⬡ | O-n-Propyl |
Examples 35–44
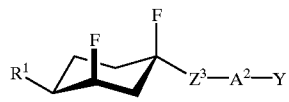
| | R¹ | Z³ | A² | Y |
|---|---|---|---|---|
| (35) | n-Pentyl | — | ⬡ (cyclohexyl) | n-Propyl |
| (36) | n-Pentyl | —CH₂—CH₂— | ⬡ (cyclohexyl) | n-Pentyl |
| (37) | n-Pentyl | — | ⬡ (cyclohexyl) | O-n-Propyl |
| (38) | n-Pentyl | — | ⬡ (cyclohexyl) | CH=CH₂ |
| (39) | n-Propyl | — | ⬡ (cyclohexyl) | trans-(CH₂)₂CH=CHCH₃ |
| (40) | n-Propyl | — | ⬡ (phenyl) | CH=CH₂ |
| (41) | n-Propyl | — | 2,3-difluorophenyl | F |

-continued
| | R¹ | Z³ | A² | Y |
|---|---|---|---|---|
| (42) | n-Pentyl | — | 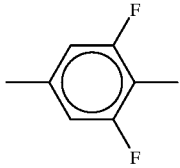 | CN |
| (43) | n-Propyl | —CH₂—CH₂— | 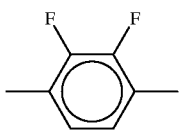 | OCF₃ |
| (44) | n-Propyl | —CH₂—CH₂— | 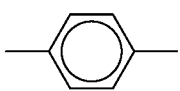 | O-n-Propyl |
Examples 45–54
| | R¹ | Z³ | A² | Y |
|---|---|---|---|---|
| (45) | n-Pentyl | — | 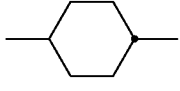 | n-Propyl |
| (46) | n-Pentyl | —CH₂—CH₂— | 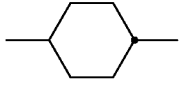 | n-Pentyl |
| (47) | n-Pentyl | — | 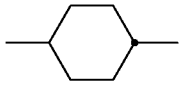 | O-n-Propyl |
| (48) | n-Pentyl | — |  | CH=CH₂ |
| (49) | n-Propyl | — | 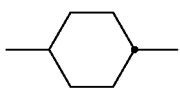 | trans-(CH₂)₂CH=CHCH₃ |
| (50) | n-Propyl | — |  | CH=CH₂ |

-continued
| | R¹ | Z³ | A² | Y |
|---|---|---|---|---|
| (51) | n-Propyl | — | 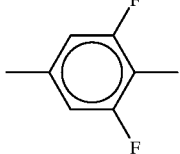 | F |
| (52) | n-Pentyl | — | 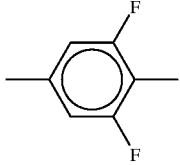 | CN |
| (53) | n-Propyl | —CH₂—CH₂— | 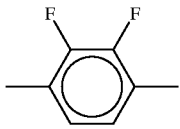 | OCF₃ |
| (54) | n-Propyl | —CH₂—CH₂— | 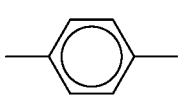 | O-n-Propyl |
Examples 55–64
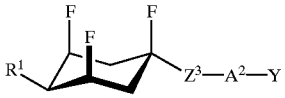
| | R¹ | Z³ | A² | Y |
|---|---|---|---|---|
| (55) | n-Pentyl | — |  | n-Propyl |
| (56) | n-Pentyl | —CH₂—CH₂— |  | n-Pentyl |
| (57) | n-Pentyl | — |  | O-n-Propyl |
| (58) | n-Pentyl | — |  | CH=CH₂ |

-continued
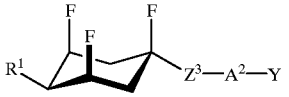
| | R¹ | Z³ | A² | Y |
|---|---|---|---|---|
| (59) | n-Propyl | — |  | trans-(CH₂)₂CH=CHCH₃ |
| (60) | n-Propyl | — |  | CH=CH₂ |
| (61) | n-Propyl | — | 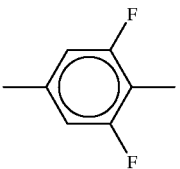 | F |
| (62) | n-Pentyl | — | 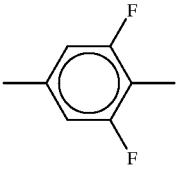 | CN |
| (63) | n-Propyl | —CH₂—CH₂— | 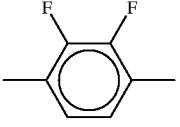 | OCF₃ |
| (64) | n-Propyl | —CH₂—CH₂— | 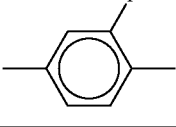 | O-n-Propyl |
Examples 65–74
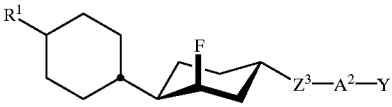
| | R¹ | Z³ | A² | Y |
|---|---|---|---|---|
| (65) | n-Pentyl | — |  | n-Propyl |
| (66) | n-Pentyl | —CH₂—CH₂— |  | n-Pentyl |

-continued
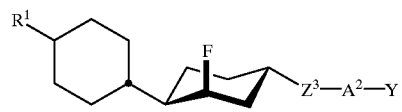
| | R¹ | Z³ | A² | Y |
|---|---|---|---|---|
| (67) | n-Pentyl | — | 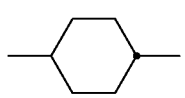 | O-n-Propyl |
| (68) | n-Pentyl | — | 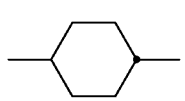 | CH=CH₂ |
| (69) | n-Propyl | — | 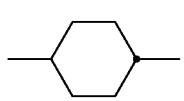 | trans-(CH₂)₂CH=CHCH₃ |
| (70) | n-Propyl | — | 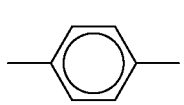 | CH=CH₂ |
| (71) | n-Propyl | —CO—O— | 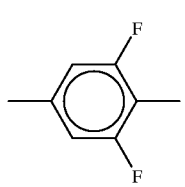 | F |
| (72) | n-Pentyl | — | 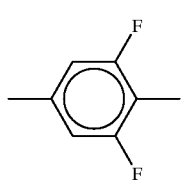 | CN |
| (73) | n-Propyl | —CH₂—CH₂— | 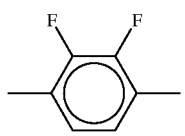 | OCF₃ |
| (74) | n-Propyl | —CH₂—CH₂— | 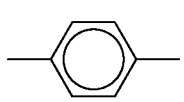 | O-n-Propyl |

Examples 75–84
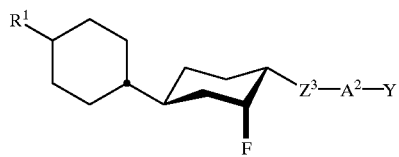
| | R[1] | Z[3] | A[2] | Y | |
|---|---|---|---|---|---|
| (75) | n-Pentyl | — | (cyclohexyl) | n-Propyl | |
| (76) | n-Pentyl | —CH$_2$—CH$_2$— | (cyclohexyl) | n-Pentyl | |
| (77) | n-Pentyl | — | (cyclohexyl) | O-n-Propyl | |
| (78) | n-Pentyl | — | (cyclohexyl) | CH=CH$_2$ | |
| (79) | n-Propyl | — | (cyclohexyl) | trans-(CH$_2$)$_2$CH=CHCH$_3$ | |
| (80) | n-Propyl | —CO—O— | (phenyl) | CH=CH$_2$ | |
| (81) | n-Propyl | — | (2,3-difluorophenyl) | F | C 112 I, Δε 11,3, Δn 0,007 |
| (82) | n-Pentyl | — | (2,3-difluorophenyl) | F | C 120 I |
| (83) | n-Propyl | —CH$_2$—CH$_2$— | (2,3-difluorophenyl) | OCF$_3$ | |
| (84) | n-Propyl | —CH$_2$—CH$_2$— | (phenyl) | O-n-Propyl | |

Examples 85–94
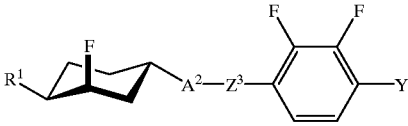
| | R¹ | Z³ | A² | Y |
|---|---|---|---|---|
| (85) | n-Pentyl | — | 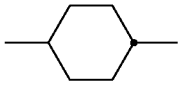 | n-Propyl |
| (86) | n-Pentyl | —CH₂—CH₂— |  | n-Pentyl |
| (87) | n-Pentyl | — |  | O-n-Propyl |
| (88) | n-Pentyl | — | 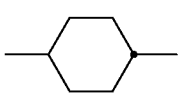 | CH=CH₂ |
| (89) | n-Propyl | — | 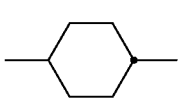 | trans-(CH₂)₂CH=CHCH₃ |
| (90) | n-Propyl | —CO—O— | 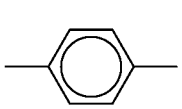 | CH=CH₂ |
| (91) | n-Propyl | — | 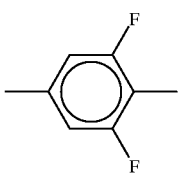 | F |
| (92) | n-Pentyl | — | 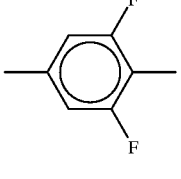 | CN |
| (93) | n-Propyl | —CH₂—CH₂— |  | OCF₃ |
| (94) | n-Propyl | —CH₂—CH₂— | 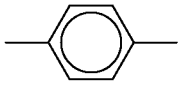 | O-n-Propyl |

Examples 95–104
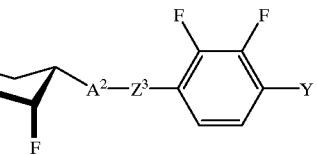
| | R¹ | Z³ | A² | Y |
|---|---|---|---|---|
| (95) | n-Pentyl | — | cyclohexyl | n-Propyl |
| (96) | n-Pentyl | —CH$_2$CH$_2$— | cyclohexyl | n-Pentyl |
| (97) | n-Pentyl | — | cyclohexyl | O-n-Propyl |
| (98) | n-Pentyl | — | cyclohexyl | CH=CH$_2$ |
| (99) | n-Propyl | — | cyclohexyl | trans-(CH$_2$)$_2$CH=CHCH$_3$ |
| (100) | n-Propyl | —CO—O— | phenyl | CH=CH$_2$ |
| (101) | n-Propyl | — | 2,6-difluorophenyl | F |
| (102) | n-Pentyl | — | 2,6-difluorophenyl | CN |
| (103) | n-Propyl | —CH$_2$—CH$_2$— | 2,3-difluorophenyl | OCF$_3$ |
| (104) | n-Propyl | —CH$_2$—CH$_2$— | phenyl | O-n-Propyl |

Examples 105–114
| | R¹ | Z² | Z³ | A² | Y |
|---|---|---|---|---|---|
| (105) | n-Pentyl | — | — | — | n-Propyl |
| (106) | n-Pentyl | —CH₂—CH₂— | — | — | n-Pentyl |
| (107) | n-Pentyl | — | — | cyclohexyl | O-n-Propyl |
| (108) | n-Pentyl | — | — | cyclohexyl | CH=CH₂ |
| (109) | n-Propyl | —CH₂—CH₂— | — | cyclohexyl | trans-(CH₂)₂CH=CHCH₃ |
| (110) | n-Propyl | —CH₂—CH₂— | — | phenyl | CH=CH₂ |
| (111) | n-Propyl | — | — | 2,3-difluorophenyl | F |
| (112) | n-Pentyl | — | — | 2,3-difluorophenyl | CN |
| (113) | n-Propyl | — | —CH₂—CH₂— | 2,3-difluorophenyl | OCF₃ |
| (114) | n-Propyl | — | —CH₂—CH₂— | phenyl | O-n-Propyl |

Examples 125–134
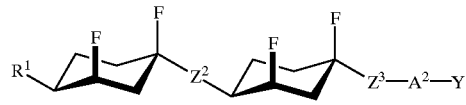
| | $R^1$ | $Z^2$ | $Z^3$ | $A^2$ | Y |
|---|---|---|---|---|---|
| (125) | n-Pentyl | — | — | — | n-Propyl |
| (126) | n-Pentyl | —CH$_2$—CH$_2$— | — | — | n-Pentyl |
| (127) | n-Pentyl | — | — | cyclohexyl | O-n-Propyl |
| (128) | n-Pentyl | — | — | cyclohexyl | CH=CH$_2$ |
| (129) | n-Propyl | —CH$_2$—CH$_2$— | — | cyclohexyl | trans-(CH$_2$)$_2$CH=CHCH$_3$ |
| (130) | n-Propyl | —CH$_2$—CH$_2$— | — | phenyl | CH=CH$_2$ |
| (131) | n-Propyl | — | — | 3,5-difluorophenyl | F |
| (132) | n-Pentyl | — | — | 3,5-difluorophenyl | CN |
| (133) | n-Propyl | — | —CH$_2$—CH$_2$— | 2,3-difluorophenyl | OCF$_3$ |
| (134) | n-Propyl | — | —CO—O— | phenyl | O-n-Propyl |

Examples 135–144
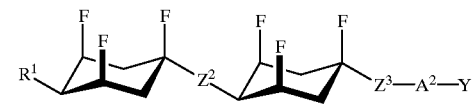
| | R¹ | Z² | Z³ | A² | Y |
|---|---|---|---|---|---|
| (135) | n-Pentyl | — | — | — | n-Propyl |
| (136) | n-Pentyl | —CH₂—CH₂— | — | — | n-Pentyl |
| (137) | n-Pentyl | — | — | cyclohexyl | O-n-Propyl |
| (138) | n-Pentyl | — | — | cyclohexyl | CH=CH₂ |
| (139) | n-Propyl | —CH₂—CH₂— | — | cyclohexyl | trans-(CH₂)₂CH=CHCH₃ |
| (140) | n-Propyl | —CH₂—CH₂— | — | phenyl | CH=CH₂ |
| (141) | n-Propyl | — | — | 2,3,5-trifluorophenyl | F |
| (142) | n-Pentyl | — | — | 2,3,5-trifluorophenyl | CN |
| (143) | n-Propyl | — | —CH₂—CH₂— | 2,3-difluorophenyl | OCF₃ |
| (144) | n-Propyl | — | —CO—O— | phenyl | O-n-Propyl |

Examples 145–149

| | R¹ | Y |
|---|---|---|
| (145) | n-Pentyl | n-Propyl |
| (146) | n-Pentyl | n-Pentyl |
| (147) | n-Pentyl | O-n-Propyl |
| (148) | n-Propyl | CH=CH$_2$ |
| (149) | n-Propyl | trans-(CH$_2$)$_2$CH=CHCH$_3$ |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A cyclohexane compound of the formula I in which

Y is alkyl or alkoxy having 1 to 10 carbon atoms which is unsubstituted or at least monosubstituted by halogen; alkenyl or alkenyloxy having 2 to 10 carbon atoms which is unsubstituted or at least monosubstituted by —CN, —CF$_3$, or —F; or is —CN, —F, —OCHF$_2$, —OCF$_3$, —OCHFCF$_3$ or —OCF$_2$CF$_3$, X$^1$, X$^2$ and X$^3$ are each independently of one another, H, F, Cl or CN in the axial position, where X$^1$ and X$^3$ are not simultaneously H, R$^1$ is H, an alkyl or alkenyl radical having 1–12 carbon atoms which is unsubstituted, monosubstituted by CN or CF$_3$ or at least monosubstituted by halogen, where one or more non-adjacent CH$_2$ groups in these radicals, in each case independently of one another, are optionally replaced by —O—, —S—, —CO—, —CO—O—, —O—CO— or —O—CO—O—, A$^1$ and A$^2$ are each independently of one another,
  a) a trans-1,4-cyclohexylene radical, in which, in addition, one or more non-adjacent CH$_2$ groups are optionally replaced by —O— and/or —S—,
  b) a 1,4-phenylene radical, in which, in addition, one or two CH groups are optionally replaced by N,
  c) a radical selected from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, or
  d) a 1,4-cyclohexenylene radical, where the radicals a), b) and d) are optionally substituted by CN, Cl or F, Z$^1$, Z$^2$ and Z$^3$ are each independently of one another, —OC—O—, —O—CO—, —CH$_2$O—, —O—, —O—CH$_2$—, —CH$_2$CH$_2$—, —CH=CH—, —C≡C— or a single bond, n and m, independently of one another, are 0, 1, 2 or 3 and P is 0, 1, 2 or 3, where m+n+p is 1, 2, 3 or 4.

2. A cyclohexane compound of the formula I according to claim 1, wherein n is 0 or 1 and m and p are 0, 1 or 2.

3. A cyclohexane compound of the formula I according to claim 1, wherein Z$^1$, Z$^2$ and Z$^3$, independently of one another, are —CH$_2$CH$_2$—, —CH=CH— or a single bond.

4. A cyclohexane compound of the formula I according to claim 1, wherein R$^1$ is a straight-chain alkyl or alkoxy having 1 to 10 carbon atoms or alkenyl having 2 to 10 carbon atoms, and Y is alkyl having 1 to 10 carbon atoms, alkenyl having 2 to 10 carbon atoms, —CN, —F, —OCHF$_2$ or —OCF$_3$.

5. A cyclohexane compound of the formula I according to claim 1, wherein the radicals R$^1$ and Y are simultaneously alkyl having 1 to 10 carbon atoms, n is 0 and m is 1.

6. A liquid-crystalline medium which comprises at least one cyclohexane compound according to claim 1.

7. A liquid-crystalline medium having at least two liquid-crystalline components, wherein at least one component is a cyclohexane compound of the formula I of claim 1.

8. A liquid-crystal display element, which contains a liquid-crystalline medium according to claim 7.

9. An electro-optical display element, which contains, as dielectric, a liquid-crystalline medium according to claim 7.

10. A liquid crystal display element according to claim 8, based on the principle of the twisted cell, the guest-host effect, the effect of deformation of aligned phases, the effect of electrically controlled birefringence or the effect of dynamic scattering.

11. A liquid crystal display element according to claim 8, which is in a TFT or STN display.

12. A liquid crystal display element according to claim 8, based on the principle of the effect of deformation of aligned phases.

13. A cyclohexane compound according to claim 1, wherein Y is —CN, —F, —OCF$_3$, a straight chain alkyl or alkoxy of 1 to 10 carbon atoms or alkenyl or alkenyloxy of 2 to 10 carbon atoms.

14. A cyclohexane compound according to claim 1, wherein at least one of X$^1$ or X$^3$ is F or CN.

15. A cyclohexane compound according to claim 1, wherein at least one of X$^1$ or X$^3$ is F.

16. A cyclohexane compound according to claim 1, wherein A$^1$ and A$^2$ are independently a 1,4-cyclohexylene, 1,4-cyclohexenylene, 1,3-dioxane-2,5-diyl, 1,4-phenylene, pyridine-2,5-diyl or pyrimidine-2,5-diyl radical.

17. A cyclohexane compound according to claim 1, wherein A$^1$ is 1,4-phenylene monosubstituted or disubstituted by F or CN.

* * * * *